United States Patent [19]

Harandi et al.

[11] Patent Number: 4,925,455
[45] Date of Patent: May 15, 1990

[54] PROCESS FOR THE ETHERIFICATION OF LINEAR AND BRANCHED OLEFINS

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 324,878

[22] Filed: Mar. 17, 1989

[51] Int. Cl.$^5$ ................................................ C10L 1/18
[52] U.S. Cl. .......................................... 44/77; 585/415; 585/417; 568/697; 568/699
[58] Field of Search ................ 44/77, 53; 585/415, 585/416, 417; 568/697, 699

[56] References Cited

U.S. PATENT DOCUMENTS 3,849,082 11/1974 Kozlowski et al.
3,912,463 10/1975 Kozlowski et al.
4,423,251 12/1983 Pujado et al.
4,503,264 3/1985 Al-Muddarris.
4,647,703 3/1987 Torck et al.
4,684,757 8/1987 Avidan et al.
4,714,787 12/1987 Bell et al.
4,826,507 5/1989 Harandi et al. ......................... 44/77
4,830,635 5/1989 Harandi et al. ......................... 44/56
4,835,329 5/1989 Harandi et al. ....................... 585/415
4,854,939 8/1989 Harandi et al. ......................... 44/77

Primary Examiner—Jacqueline V. Howard
Attorney, Agent, or Firm—Alexander J. McKillop; Charles J. Speciale; L. G. Wise

[57] ABSTRACT

A process is disclosed for converting a light hydrocarbon feedstock that contains a mixture of linear and branched olefins to ether-rich high octane gasoline streams that include tertiary alkyl and isoalkyl ethers such as MTBE, TAME, methyl isopropyl ether (MIPE), and methyl sec-butylether (MSBE). Further, it has been discovered that, following etherification unreacted paraffins in the process can be dehydrogenated to produce $C_3$–$C_4$ olefins which can be recycled to the etherification process. The conversion is achieved by utilizing the differing reactivity of tertiary olefins under selected conditions compared to linear olefins in the catalyzed etherification processes. The process integrates a first stage tertiary olefin etherification, separation of ether-rich gasoline and a second stage linear olefin etherification to produce a second ether rich gasoline stream.

15 Claims, 2 Drawing Sheets

MIXED OLEFINS CONVERSION TO ETHERS

MIXED OLEFINS CONVERSION TO ETHERS

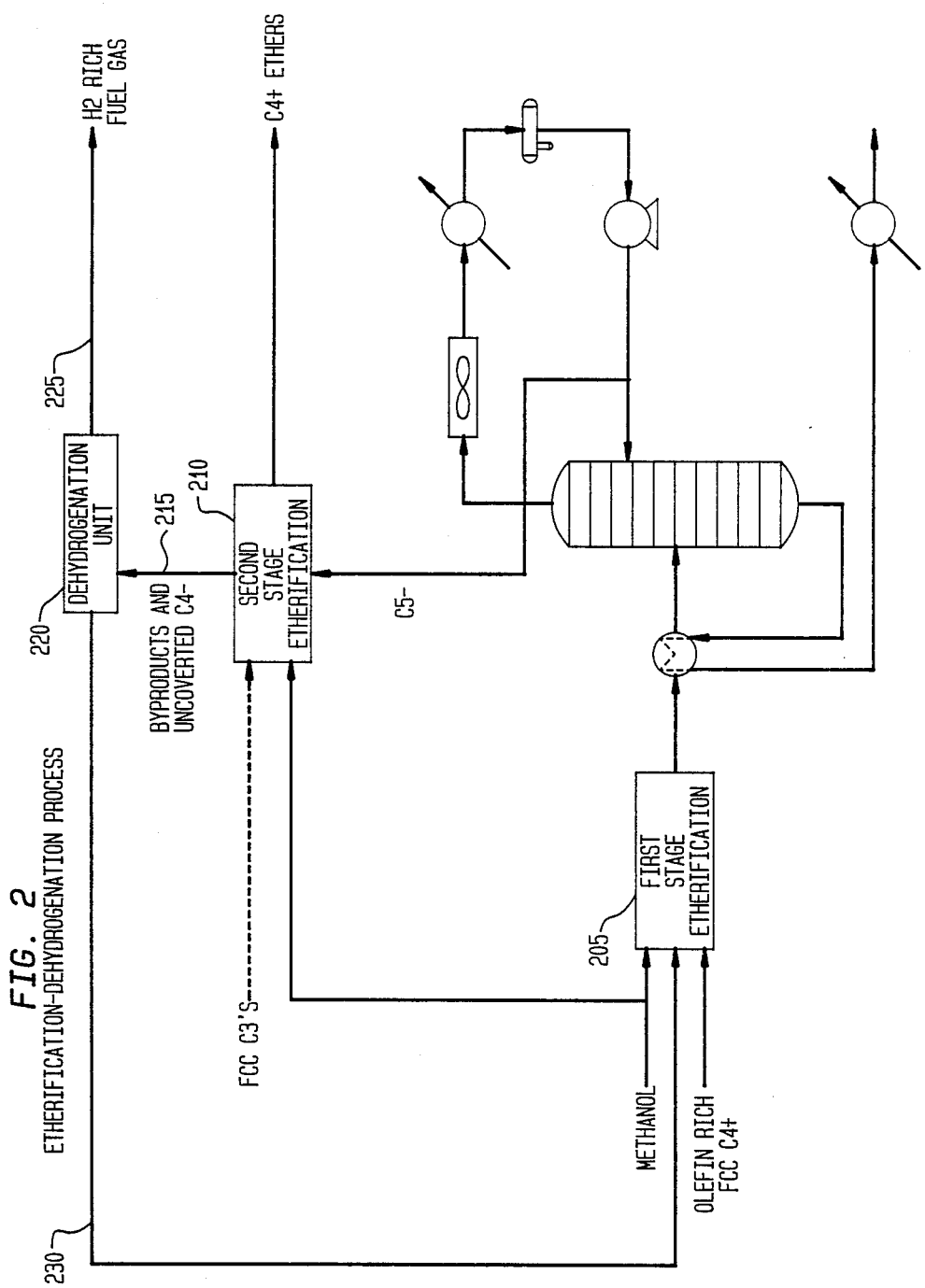

PROCESS FOR THE ETHERIFICATION OF LINEAR AND BRANCHED OLEFINS

This invention relates to a process for the conversion of mixed linear and branched olefins to ethers. More particularly, the invention relates to a process for the conversion of a hydrocarbon feedstream containing light linear and branched olefins to ether rich gasoline. The invention, more specifically, pertains to the manufacture of gasoline containing methyl tertiary butyl ether (MTBE) and tertiary amyl methyl ether (TAME) plus lower isoalkyl ethers.

BACKGROUND OF THE INVENTION

A comparatively recent development in the petroleum arts is the use of $C_5$–$C_7$ methyl alkyl ethers, especially methyl tertiary butyl ether (MTBE) and tertiary amyl methyl ether (TAME) for enhancing gasoline octane. It is known that alkyl tert-alkyl ethers can be prepared by reacting a primary alcohol with an olefin having a double bond on a tertiary carbon atom, thus methanol reacts with isobutylene and isopentenes (2 methyl 1-butene or 2 methyl 2-butene) to form respectively methyl tert-butyl ether (MTBE) and methyl tert-amyl ether (MTAE). The reaction is selective for tertiary olefins so that it constitutes a valid process for their removal from olefinic streams in which they are contained together with linear unreactive olefins. The reaction has an equilibrium which is favorable to the synthesis of the ether as the reaction temperature is lowered, in accordance with the reactions negative enthalpy.

It is known that the reaction is catalyzed by Lewis acids (aluminum trichloride, boron trifluoride), mineral acids (sulfuric acid) and organic acids (alkyl and aryl sulfonic acids, ion exchange resins). Particularly suitable for the task are ion exchange resins in their acid form and it is known that the best results are obtained by means of macroreticular resins of the type "Amberlyst 15". By means of such last named catalysts it is possible to reach thermodynamic equilibrium within industrially acceptable contact times in the temperature range of 50°–60° C.

U.S. Pat No. 4,262,145 to Selwitz et al. discloses the catalytic reaction of a branched olefin such as isobutylene, 2-methylpentene-2, 2-methylbutene-2, and 2,3-dimethyloctene-2 with a lower alkanol such as methanol to form a mixed ether such as methyl tert-butyl ether. The catalyst disclosed is silicotungstic acid.

A process is also known for manufacturing ethers from linear mono-olefins, thereby augmenting the supply of high octane blending stock for gasoline. The lower molecular weight ethers, such as methyl isopropyl ether, are in the gasoline boiling range and are known to have a high blending octane number.

U.S. Pat. No. 4,714,787 to Bell et al., incorporated herein by reference in its entirety, provides a catalytic process for selectively reacting one or more linear monoolefins with a primary or secondary lower molecular weight alcohol to form the corresponding ether. The active acidic catalyst component for the process is selected from the group consisting of sulfonated ion-exchange resins and crystalline silicates having a pore size greater than 5 A.U. Of the crystalline silicates, those preferred include crystalline zeolites having a silica to alumina mol ratio greater than about 12. In a particularly preferred embodiment, methanol and propylene are reacted to selectively form methyl isopropyl ether (MIPE).

A preferred feedstock for the manufacture of MTBE and TAME in petroleum refinery operations is the light hydrocarbon stream from FCC operations. These streams are rich in $C_4+$ tertiary olefins such as isobutylene. However, they also contain significant amounts of linear olefins plus linear and branched paraffins. The linear olefins, particularly propylene and 1-butene, are not etherified in the prior art MTBE processes. Conventionally, these linear unreacted olefins are carried through the process and separated downstream. In this regard they represent a burden on the volumetric effectiveness of the etherification process, providing no contribution to the production of ether-rich high octane gasoline.

Accordingly, it is an object of the present invention to provide a process for the enhanced conversion of hydrocarbon streams containing mixed branched and linear olefins to ether-rich high octane gasoline.

It is another object of the present invention to provide an integrated process for the sequential conversion of tertiary olefins and linear olefins to lower alkyl ethers.

Yet another object of the instant invention is to provide an integrated process for converting hydrocarbon feedstock comprising mixed olefins and paraffins to high octane ethers and gasoline.

SUMMARY OF THE INVENTION

It has been discovered that a light hydrocarbon feedstock that contains a mixture of linear and branched olefins can be converted to ether-rich high octane gasoline streams that include tertiary alkyl and isoalkyl ethers such as MTBE, TAME, methyl isopropyl ether (MIPE), and methyl sec-butylether (MSBE). Further, it has been discovered that unreacted paraffins in the process can be dehydrogenated to produce $C_3$–$C_4$ olefins which can be recycled to the etherification process. The conversion is achieved by utilizing the differing reactivity of tertiary olefins under selected conditions compared to linear olefins in the catalyzed etherification processes.

More particularly, an integrated once through process has been discovered for the production of ether-rich liquid fuels, comprising: contacting a fresh mixture of excess lower alkyl alcohol and a light hydrocarbon feedstock containing linear olefins and $C_4+$ tertiary olefins with an acidic etherification catalyst in a first etherification zone under tertiary olefin etherification conditions whereby an etherification effluent stream containing lower alkyl tertiary alkyl ethers is produced. The etherification effluent stream is separated to provide a first stream comprising ether-rich $C_5+$ gasoline and a second stream comprising unreacted lower alkyl alcohol and linear olefinic $C_5-$ hydrocarbons. The second stream is contacted with an acidic metallosilicate catalyst in a second etherification zone under conditions effective to etherify said linear olefinic hydrocarbons. The $C_5+$ ether-rich gasoline is recovered plus unreacted lower alcohol and hydrocarbons from said second etherification zone.

The invention also includes the further steps of passing unreacted hydrocarbons from the second etherification zone to a dehydrogenation zone under paraffins dehydrogenation conditions whereby $C_4$ olefins are produced and hydrogen rich fuel gas. The $C_4$ olefins are recycled to the first etherification zone in conjunction with light hydrocarbon feedstock.

DESCRIPTION OF THE DRAWINGS

FIG. 2 is a schematic drawing of the present invention incorporating dehydrogenation.

DETAILED DESCRIPTION OF THE INVENTION

Figure 1:
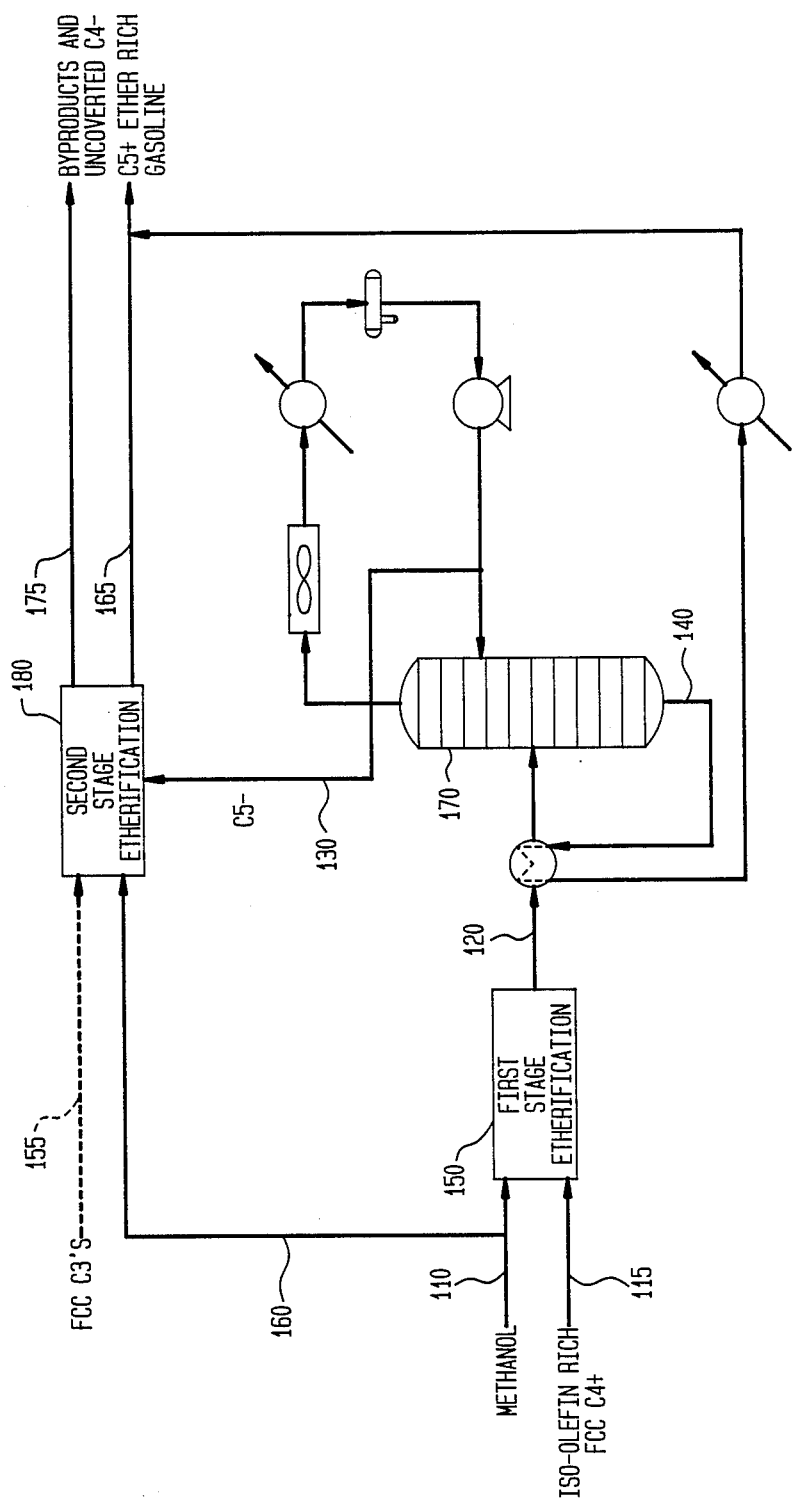
FIG. 1 is a schematic drawing of a preferred embodiment of the present invention.

In the preferred embodiments of this invention lower alkanol such as methanol, ethanol or isopropanol is reacted with hydrocarbon feedstock containing mixed olefins in a serially integrated process to etherify both branched and linear olefins and produce high octane gasoline. The olefins of particular interest are tertiary olefins such as isobutylene, to produce tertiary alkyl ethers, particularly methyl tertiary butyl ether and methyl tertiary amyl ether. $C_3$–$C_4$ linear olefins are converted to lower alkyl isopropyl ether and sec-butyl ether. Preferred ethers from linear olefins are methyl isopropyl ether and methyl sec-butyl ether. In the etherification reaction, methanol is generally present in an excess amount between 2 wt. % to 100 wt. %, based upon converted tertiary olefins. Following a first etherification reaction, the etherification reaction effluent stream, which comprises unreacted alkanol, hydrocarbons including a major portion of $C_4+$ hydrocarbons containing unreacted linear olefins and methyl tertiary alkyl ethers, is separated to produce $C_5+$ gasoline rich in tertiary alkyl ethers and a hydrocarbon stream containing linear olefins for further etherification in a second etherification reaction.

Methanol is the preferred lower alcohol used in the present invention. Methanol may be readily obtained from coal by gasification to synthesis gas and conversion of the synthesis gas to methanol by well-established industrial processes. As an alternative, methanol may be obtained from natural gas by other conventional processes, such as steam reforming or partial oridation to make the intermediate syngas. Crude methanol from such processes usually contains a significant amount of water, usually in the range of 4 to 20 wt %. Water in the feed to the second etherification stage reacts with olefins to form alcohols, e.g. t-butanol, isopropanol and sec-butanol, which can be further reacted to produce ethers. The etherification catalyst employed for tertiary olefin etherification is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites. Typical hydrocarbon feedstock materials for etherification reactions include olefinic streams, such as FCC light naphtha and butenes rich in iso-olefins. These aliphatic streams are produced petroleum refineries by catalytic cracking of gas oil or the like.

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Boosting Combo," by J. D. Chase, et al., *The Oil and Gas Journal*, Apr. 9, 1979, pages 149–152, discusses the technology. A typical acid catalyst is Amberlyst 15 sulfonic acid resin from Rohm and Haas Co.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added base fuel (R+O=91) is about 120. For a fuel with a motor rating (M+O=83) octane, the blending value of MTBE at the 10% level is about 103. On the other hand, for an (R+O) of 95 octane fuel, the blending value of 10% MTBE is about 114.

Processes for producing and recovering MTBE and other methyl tertiary alkyl ethers from $C_4$–$C_7$ isoolefins are known to those skilled in the art, such as disclosed in U.S. Pat. Nos. 4,544,776 (Osterburg, et al.) and 4,603,225 (Colaianne et al.). Various suitable extraction and distillation techniques are known for recovering ether and hydrocarbon streams from etherification effluent.

The process of this invention is based on the integration of the above tertiary olefin etherification with the known process that linear monoolefins, under the proper reaction conditions, react in the presence of a solid insoluble acid catalyst with a low molecular weight primary or secondary monohydric alcohol to selectively produce ethers. In the process, unconverted isobutene from the first etherification zone is partially converted to MTBE in the second etherification zone.

Linear monoolefins and mixtures thereof useful in the process of this invention include, broadly, those having 3 to 15 carbon atoms, and these have the structure

$$R_1-CH=CH-R_2$$

wherein $R_1$ and $R_2$ individually are hydrogen or alkyl groups and the total carbon atoms $R_1$ plus $R_2$ is from 1 to 13. However, in a preferred embodiment of the present invention, the preferred linear olefins are those having 3 to 5 carbon atoms, i.e. the total carbon atoms in $R_1$ plus $R_2$ is 1 to 3. Particularly preferred feed is propylene, 1-butene and 2-butene.

Although the hydrocarbon feed to the process may be substantially linear olefin (i.e. greater than 90 wt % of olefin), it is a feature of the invention that the reaction proceeds well in the presence of paraffin.

The alcohol to be reacted with the linear olefin is any primary or secondary alcohol having up to 4 carbon atoms. These include the primary alcohols methanol, ethanol, n-propanol, n-butanol and isobutanol; and the secondary alcohols isopropanol and sec-butanol. The lower alcohols are preferred, with methanol being particularly preferred.

The process of this invention may be conducted batchwise. However, it is generally advantageous, and therefore preferred, to conduct the process as a continuous operation. Since the linear olefin etherification reaction is exothermic, temperature control is facilitated by a continuous cascade operation with two or more reactors in sequence and with interstage cooling. Operable reaction conditions are given in Table I for linear olefin etherification. The weight hourly space velocity (WHSV) referred to in Table I and elsewhere herein, unless explicitly stated to be otherwise, is based on reactants, i.e. the total weight of linear olefin plus alcohol divided by the total weight of binder-free insoluble acid catalyst per hour. The corresponding contact times, of course, apply to batch conversions.

TABLE 1

| | Reaction Conditions | | | |
|---|---|---|---|---|
| | Mol Ratio alcohol/olefin | Temp. °C. | Press. atm. | WHSV Hr$^{-1}$ |
| Broad | 0.1–10 | 50–300 | 1.0–300 | 0.05–50 |
| Preferred | 0.3–3 | 80–250 | 5–200 | 0.2–20 |
| Most Preferred | 0.5–2 | 100–210 | 10–100 | 0.5–10 |

The principal ether product or products produced depends on the linear olefin and the alcohol charged. In the case of methanol and propylene, for example, the principal reaction product is methyl isopropyl ether. With butene-1 or the cis- or trans-butene-2, methyl sec-butyl ether is formed. In brief, the ethers formed are those predicted by the Markovnikov rule for addition to the double bond of the linear olefin. In the case of the higher molecular weight linear monoolefins, or mixtures of olefins, the principal reaction product is a mixture of such ethers.

The principal by-products formed in the conversion are the ether and water resulting from the autocondensation of the alcohol charged. Other by-products include alcohol resulting from the hydration of the linear monoolefin, and the ether formed by the self-condensation of the latter alcohol. Also formed is a small amount of hydrocarbon believed to be the oligomer of the olefin charged. This hydrocarbon by-product appears to account for less than 5 wt % of the total olefin converted under moderate temperatures, such as at a temperature not higher than about 160° C.

The new process of this invention for manufacturing ether-rich gasolines from refinery feedstock such as FCC naphtha utilizes a two stage etherification system including an interstage separation section as shown in FIG. 1. The first stage etherification preferably operates at a relatively low temperature (37°-93° C.) in order to efficiently convert tertiary olefins, i.e., olefins wherein the double bond includes a terrtiary carbon atom, to high octane alkyl tertiary-alkyl ethers. The second etherification stage converts the first stage reactor excess alcohol, unconverted tertiary C4–C5's, and linear-/iso C5$^-$ olefins to alkyl tertiary alkyl ethers and alkyl sec-alkyl ethers, respectively. The second stage operates at a higher temperature (preferably 50°-300° C.). The preferred catalysts include Amberlyst 15 in the first stage and zeolite Beta in the second stage. The first stage preferably consists of a single fixed bed reactor in which the extent of reaction is at least 65% of equilibrium.

In another embodiment of the present invention the C5$^-$ effluent from the second stage etherification after separation of C4+ ether-rich gasoline is passed to a dehydrogenation zone and paraffins converted to olefins. The olefins so formed are recycled to the first etherification zone. It has been established that the conversion of paraffins, such as propane and butane, to mono-olefins, such as propylene and butylene, can be accomplished by thermal or catalytic dehydrogenation. A general discussion of thermal dehydrogenation (i.e., steam cracking) is presented in *Encyclopedia of Chemical Technology*, Ed. by Kirk and Othmer, Vol. 19, 1982, Third Ed., pp. 232–235. Various processes for catalytic dehydrogenation are available in the prior art. These processes include the Houdry Catofin process of Air Products and Chemical, Inc., Allentown, Pa., the Oleflex process of UOP, Inc., Des Plaines, Ill. and a process disclosed by U.S. Pat. No. 4,191,846 to Farha, Jr. et al. The Houdry Catofin process, described in a magazine article, "Dehydrogenation Links LPG to More Octanes", Gussow et al, *Oil and Gas Journal*, Dec. 8, 1980, involves a fixed bed, multi-reactor catalytic process for conversion of paraffins to olefins. Typically, the process runs at low pressures of 5–30 inches of mercury absolute, and high temperatures with hot reactor effluent at 550°-650° C. Dehydrogenation is an endothermic reaction, so it normally requires a furnace to provide heat to a feed stream prior to feeding the feed stream into the reactors. The UOP Oleflex process, disclosed in an article "$C_2/C_5$ *Dehydrogenation Undated*", Verrow et al, *Hydrocarbon Processing*, April 1982, used stacked catalytic reactors. U.S. Pat. No. 4,191,846 to Farha, Jr. et al teaches the use of group VIII metal containing catalysts to promote catalytic dehydrogenation of paraffins to olefins.

Referring now to FIG. 1 of the present invention, the integrated process of the present invention is illustrated in a flow schematic. Methanol and hydrocarbon reactants are passed to the first etherification reactor 150 in conduits 110 and 115. Preferably the hydrocarbon feed is rich in isoalkenes and also contains other paraffinic and linear olefinic hydrocarbons. The methanol feed to the first etherification zone is dry while methanol feed to the second etherification zone can be wet. Zeolite in the second etherification zone is not sensitive to water which reacts to form alcohols, R—OH. By virtue of the discovery embodied in the instant invention, the quantity of methanol passed to the etherification unit can be between 3 and 100 percent in excess of the stoichiometric amount that reacts with isoalkenes in an etherification reaction. Etherification is conducted as described heretofore and the etherification product is passed as an effluent stream to separator 170. Methanol is separated overhead preferably as an azeotropic mixture with $C_5-$ paraffinic and olefinic hydrocarbons which are passed 130 to a second etherification zone 180. A bottom fraction is withdrawn from separator 170 through conduit 140 which contains methyl tertiary alkyl etherates, such as MTBE and TAME, in admixture with $C_5+$ gasoline. The gasoline separated exhibits a high motor octane value and high research octane value. In the second etherification zone 180 linear olefins are converted to methyl ethers, optionally with added methanol from conduit 160 or $C_5$ hydrocarbons through conduit 155. Product $C_5+$ gasoline rich in ethers is separated through conduit 165 while byproducts and unconverted $C_4-$ hydrocarbons are recovered through conduit 175.

Referring now to FIG. 2, another embodiment of the present invention is presented. Byproducts and unconverted $C_4-$ hydrocarbons containing paraffins from etherification reactor 210 are passed 215 to a dehydrogenation zone 220. There, under typical paraffin dehydrogenation conditions known in the art, paraffins are converted to olefins and byproduct hydrogen rich fuel gas 225. $C_4$ olefins are separated from the dehydrogenation product and passed to the first etherification zone 205 by conduit 230 for further conversion to ethers. By-product dimethylether and methanol from the integrated process can be passed to the dehydrogenation zone where they will react exothermically and provide a portion of the heat of reaction.

Although the present invention has been described with preferred embodiments and examples, it is to be understood that modifications and variations may be resorted to without departing from the spirit and scope of this invention, as those skilled in the art will readily understand. Such modifications and variations are considered to be within the purview and scope of the appended claims.

What is claimed is:

1. An integrated once through process for the production of ether-rich liquid fuels, comprising;
    (a) contacting a fresh mixture of excess lower alkyl alcohol and a light hydrocarbon feedstock containing linear olefins and $C_4+$ tertiary olefins with an acidic etherification catalyst in a first etherification zone under tertiary olefin etherification conditions whereby an etherification effluent stream containing lower alkyl tertiary alkyl ethers is produced;
    (b) separating said etherification effluent stream to provide a first stream comprising ether-rich $C_5+$ gasoline and a second stream comprising unreacted lower alkyl alcohol and linear olefinic $C_5-$ hydrocarbons;
    (c) contacting said second stream with an acidic metallosilicate catalyst in a second etherification zone under conditions effective to etherify said linear olefinic hydrocarbons; and
    (d) recovering $C_5+$ ether-rich gasoline and unreacted hydrocarbons from said second etherification zone.

2. The process of claim 1 including the step of introducing a fresh stream of lower alkyl alcohol to step (c) etherification zone.

3. The process of claim 1 including the further step of introducing a fresh stream of $C_3$ hydrocarbons to step (c) etherification zone.

4. The process of claim 1 wherein step (a) etherification conditions comprise a high excess of said lower alkyl alcohol over $C_4+$ tertiary olefins whereby the etherification reaction equilibrium is shifted substantially toward the formation of $C_5+$ ethers.

5. The process of claim 4 wherein said excess of lower alkyl alcohol is between about 3 and 100 percent.

6. The process of claim 4 wherein said excess of lower alkyl alcohol is about 5 percent.

7. The process of claim 1 wherein said lower alkyl alcohol comprises methanol and said lower alkyl tertiary alkyl ethers comprise methyl tertiary butyl ether and tertiary amyl methyl ether.

8. The process of claim 1 wherein said metallosilicate catalyst comprises a shape-selective, acid aluminosilicate zeolite-type catalyst having the structure of zeolite Beta.

9. The process of claim 1 wherein step (c) etherified linear olefins comprise methyl isopropyl ether and methyl sec-butyl ether.

10. The process of claim 1 wherein said first zone etherification conditions comprise temperature between 37° and 93° C. and said second zone conditions comprise temperature between 50° and 300° C.

11. The process of claim 1 including the further steps of:
    passing step (c) unreacted hydrocarbons to a dehydrogenation zone under paraffins dehydrogenation conditions whereby $C_4$ olefins are produced and hydrogen rich fuel gas; and
    passing said $C_4$ olefins to step (a) etherification zone in conjunction with said light hydrocarbon feedstock.

12. The process of claim 1 wherein said metallosilicate comprises zeolite ZSM-5.

13. In the process for the production of methyl tertiary alkyl ethers comprising reacting a mixture comprising excess methanol and $C_4+$ hydrocarbons containing tertiary and linear olefins in contact with acid etherification catalyst under etherification conditions in an isoolefins etherification zone to produce a product stream comprising $C_5+$ methyl tertiary alkyl ethers, unreacted methanol and $C_5-$ hydrocarbons containing linear olefins; separating said product stream into unreacted methanol, unreacted $C_5-$ hydrocarbons and $C_5+$ ethers, recycling unreacted methanol and recovering a hydrocarbon stream rich in $C_5+$ methyl tertiary alkyl ethers, the improvement comprising:
    contacting said unreacted $C_5-$ hydrocarbons with an acidic catalyst in a second etherification zone under conditions effective to etherify said linear olefinic hydrocarbons; and
    recovering $C_5+$ ether-rich gasoline and unreacted hydrocarbons from said second etherification zone.

14. The process of claim 13 wherein said second zone catalyst comprises a shape-selective, acid aluminosilicate zeolite-type catalyst having the structure of zeolite Beta.

15. The process of claim 13 wherein said isoolefins etherification conditions comprise temperature between 37° and 93° C. and said second zone conditions comprise temperature between 50° and 300° C.

* * * * *